United States Patent [19]
Grooms et al.

[11] Patent Number: 6,045,554
[45] Date of Patent: Apr. 4, 2000

[54] CORTICAL BONE INTERFERENCE SCREW

[75] Inventors: James N. Grooms, Gainesville; Kevin Carter, High Springs; David H. Dulebohn, Naples, all of Fla.

[73] Assignee: University of Florida Tissue Bank, Inc., Alachua, Fla.

[21] Appl. No.: 09/098,916

[22] Filed: Jun. 17, 1998

Related U.S. Application Data

[62] Division of application No. 08/687,018, Jul. 16, 1996, abandoned.

[51] Int. Cl.$^7$ .................................................. A61B 17/86
[52] U.S. Cl. ................................. 606/73; 606/76; 623/13
[58] Field of Search ........................... 606/65, 72, 73, 606/88, 76; 623/16, 13; 411/402, 410

[56] References Cited

U.S. PATENT DOCUMENTS

| Re. 34,871 | 3/1995  | McGuire et al. . |
|------------|---------|------------------|
| 55,524     | 6/1866  | Morris .         |
| 846,981    | 3/1907  | Claiborne, Jr. . |
| 1,330,098  | 2/1920  | Smith .          |
| 2,570,465  | 10/1951 | Lundholm .       |
| 3,470,786  | 10/1969 | Martins .        |
| 4,171,662  | 10/1979 | Simone et al. .  |
| 4,450,835  | 5/1984  | Asnis et al. .   |
| 4,537,185  | 8/1985  | Stednitz .       |
| 4,605,414  | 8/1986  | Czaika .         |
| 4,877,020  | 10/1989 | Vich .           |
| 4,950,270  | 8/1990  | Bowman et al. .  |
| 5,282,802  | 2/1994  | Mahony, III .    |
| 5,360,448  | 11/1994 | Thramann .       |
| 5,364,400  | 11/1994 | Rego, Jr. et al. . |
| 5,378,101  | 1/1995  | Olson et al. .   |
| 5,383,878  | 1/1995  | Roger et al. .   |
| 5,470,334  | 11/1995 | Ross et al. .    |

OTHER PUBLICATIONS

Lambert, K., Vascularized Patellar Tendon Graft with Rigid . . . Clinical Orthopaedics 172:85–89, 1983.

Obwegeser, J., Bioconvertible screws made of allogenic . . . J. Cranio–Maxillo–Facial Surgery 22:63–75, 1994.

Albee, F.H. et al. (1940) "The General Principles of Bone Grafting" Bone Graft Surgery in Disease, Injury and Deformity, Appleton–Century Company, Inc. (publisher), pages xi–xv; 1–31; 48–107; and 210–227.

Zou, D. et al. (1991) "Interference Screw Fixation of Cervical Grafts: A Biomechanical Study of a New Method of Cervical Fixation" Journal of Spinal Disorders 4(2):168–176.

Matthews, L.S., S.R. Soffer (1989) "Pitfalls in the Use of Interference Screws for Anterior Cruciate Ligament Reconstruction: Brief Report" Anthroscopy: The Journal of Arthroscopic and Related Surgery 5(3):225–226.

Barrett, G.R. et al. (1995) "Endobutton Button Endoscopic Fixation Technique in Anterior Cruciate Ligament Reconstruction" Anthroscopy: The Journal of Arthroscopic and Related Surgery 11(3):340–343.

(List continued on next page.)

*Primary Examiner*—Michael Buiz
*Assistant Examiner*—David O. Reid
*Attorney, Agent, or Firm*—Gerard H. Bencen; Timothy H. Van Dyke; Bencen & Van Dyke, P.A.

[57] ABSTRACT

An interference screw is provided by machining a fragment of autograft or allograft cortical bone from a donor or from a recipient's amputated bone. The interference screw has a cortical surface into which a self-tapping thread is machined. The interference screw has a machined pointed, rounded or flush end and an opposite machined end which mates with a drive means, and has advantages over conventional interference screws known in the art in that subsequent to implantation, no residual hardware that must later be removed remains at the implant site.

3 Claims, 16 Drawing Sheets

OTHER PUBLICATIONS

Kousa, P. et al. (1995) "Fixation Strength of a Biodegradable Screw in Anterior Cruciate Ligament Reconstruction" The Journal of Bone and Joint Surgery 77–B(6):901–905.

Lemos, M.J. et al. (1995) "Assessment of Initial Fixation of Endoscopic Interference Femoral Screws with Divergent and Parallel Placement" Arthroscopy: The Journal of Arthroscopic and Related Surgery 11(1):37–41.

Kohn, D., C. Rose (1994) "Primary Stability of Interference Screw Fixation" The American Journal of Sports Medicine 22(3):334–338.

Firer, P. (1991) "In Vivo Effectiveness of Interference Screw Fixation for Bone–Ligament–Bone Anterior Curciate Ligament Reconstruction" American Journal of Sports Medicine 19(5):538–539.

Buchardt, H. (1983) "The Biology of Bone Graft Repair" Clinical Orthopaedic and Related Research 174:28–42.

Vich, J.M.O. (1985) "Anterior cervical interbody fusion with threaded cylindrical bone" J. Neurosurg. 63:750–753.

Meister, K. et al. (1996) "Allograft Bone Interference Screws in ACL Reconstructions" American Academy of Orthopaedic Surgeons 63rd Annual Meeting, Feb. 22–26, 1996 (abstract).

Albee, F.H. (1940) "Bone Graft Surgery in Disease, Injury and Deformity" D. Appleton–Century Company, Inc., pp. 20–23.

Boden, S.D. et al. (1995) "Biologic Enhancement of Spinal Fusion" Spine 20(24S):113S–123S.

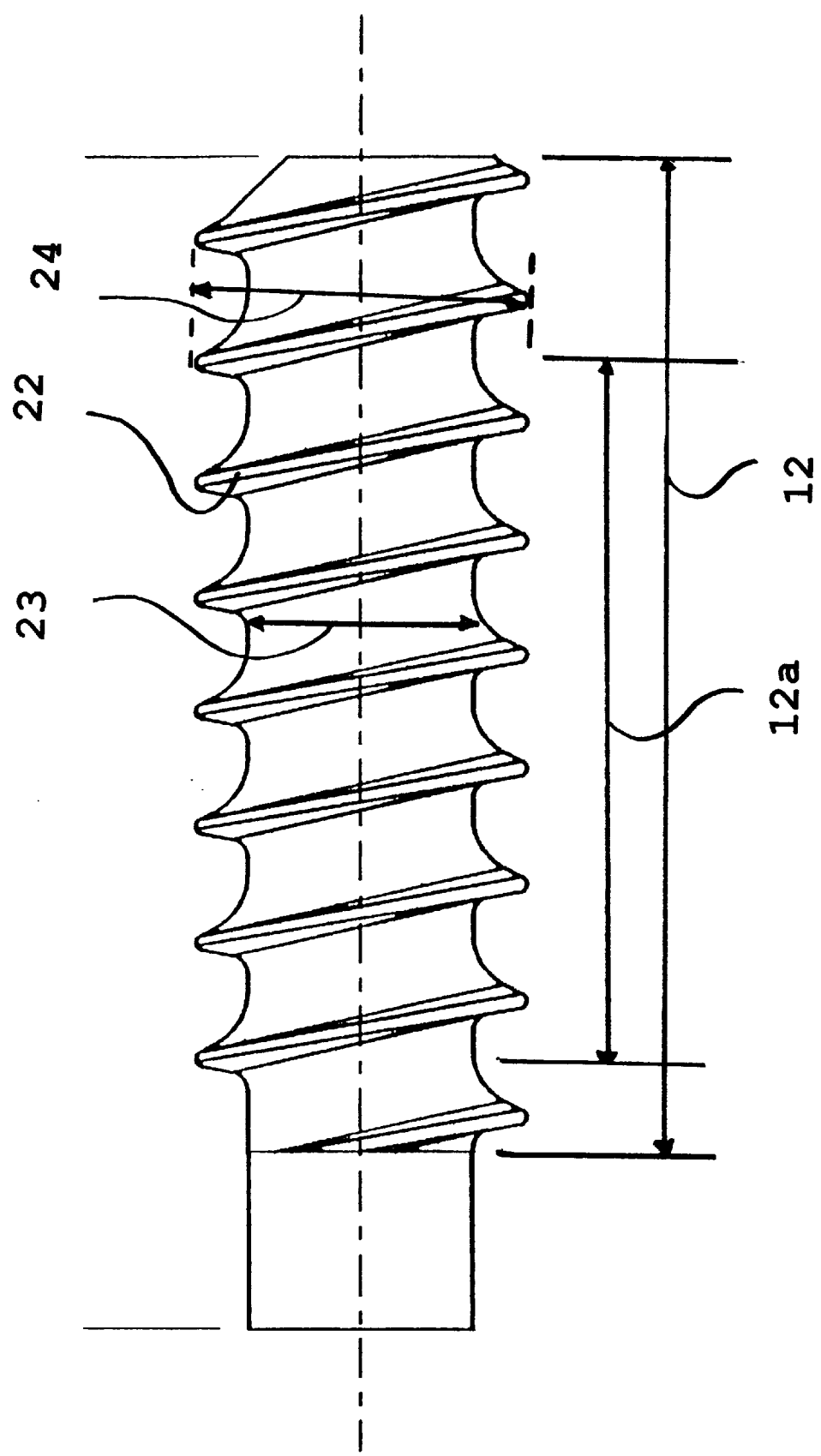

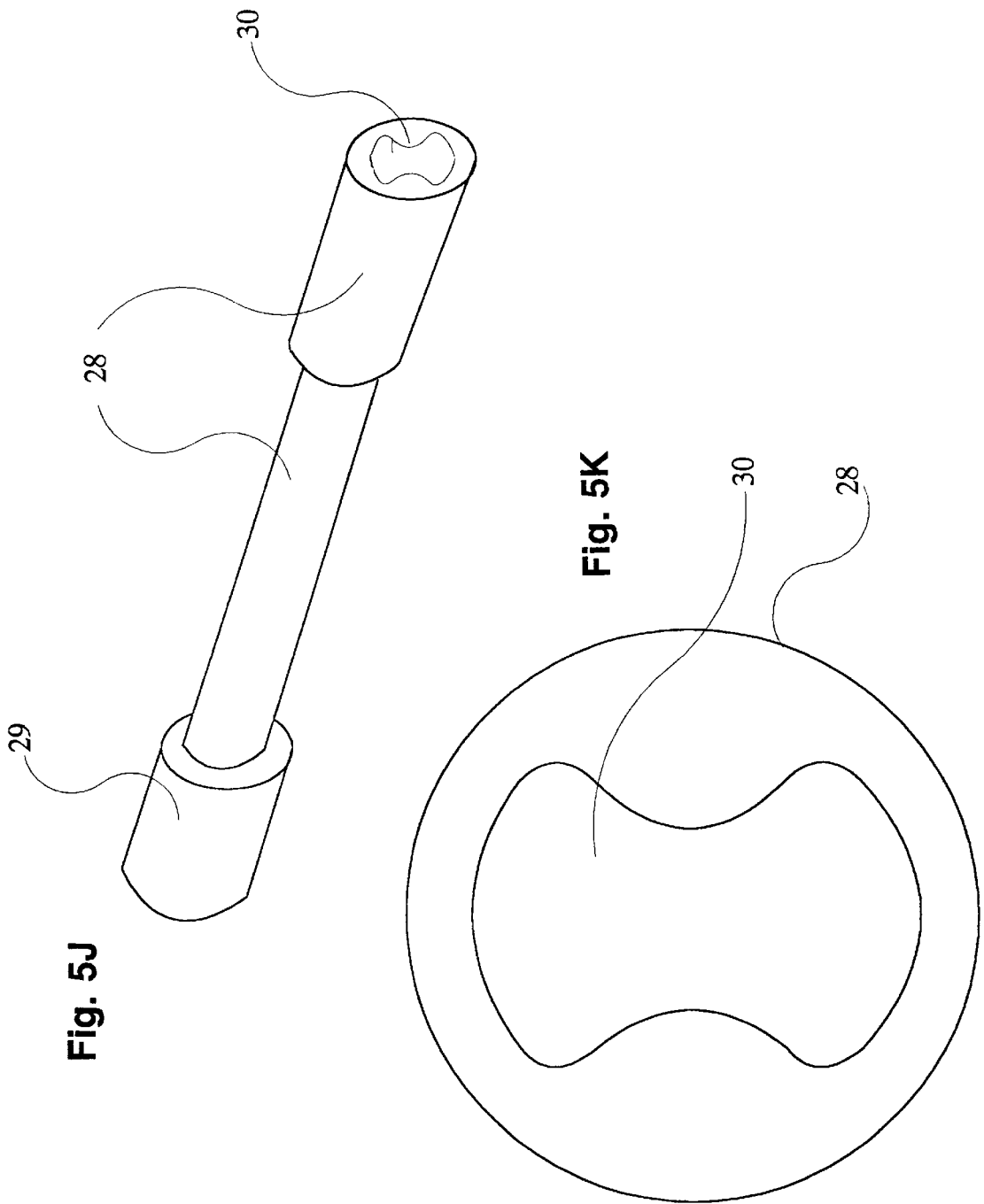

CORTICAL BONE INTERFERENCE SCREW

This application is a divisional of U.S. patent application Ser. No. 08/687,018, filed Jul. 16, 1996, which was refiled as a Continued Prosecution Application on Apr. 10, 1998, abandoned.

BACKGROUND OF THE INVENTION i. Field of the invention

This invention relates to a novel interference screw made of bone and methods of use thereof in the field of orthopaedics.

ii. Background Art

Adequate fixation of graft material is one of the more important factors in successful outcome of cruciate ligament reconstruction. Numerous methods of graft fixation have been employed, including screw and washer, staples, buttons, and interference screws. Potential problems with residual hardware include chronic pain, migration, and loss of bone stock.

A number of interference screws are known in the art for use in fixation of cervical grafts (Zou et al, 1991) anterior cruciate ligaments (Matthews et al., 1989; Barrett et al., 1995; Kousa et a., 1995; Lemos et al., 1995; Kohn et al., 1994; Firer, P, 1991). In all of these studies, metallic or synthetic interference screws were utilized. Several such screws have been patented. Thus, for example, U.S. Pat. Nos. 5,470,334 (bioabsorbable synthetic interference bone fixation screw); 5,364,400 (synthetic biocompatible interference implant); 5,360,448 (porous-coated bone screw for securing prosthesis); 5,282,802 (use of an interference fixation screw made of a material that is soft compared to bone), describe various interference screws. As pointed out in several of these documents, metallic interference screws have the disadvantage of being made from a foreign substance which is not bioabsorbed and which therefore has the potential of long-term irritation and other complications. The synthetic interference screws likewise have a number of problems, even though allegedly being bioabsorbable. For example, there are difficulties in obtaining materials with sufficient rigidity and strength that are bioabsorbable. In addition, since the known synthetic bioabsorbable interference screws are not made of bone, they do not contribute to bone mass once they are bioabsorbed. None of these documents disclose an interference screw which itself is made from cortical bone.

Dr. J. M. Otero Vich published an article in 1985 relating to an "Anterior cervical interbody fusion with threaded cylindrical bone", (Vich, J. M., 1985), in which a modified Cloward dowel made from autologous or heterologous bone is described. Whereas the standard Cloward type dowel for cervical interbody fusion is a cylindrical dowel of bone taken from the iliac crest, Dr. Vich disclosed a technique in which there is required "the intraoperative threading of the cylindrical bone graft (either autologous or heterologous) to be implanted into the appropriate intervertebral space". Screw threads were placed in the graft with a small, previously sterilized die, and the graft was then screwed into a cylindrical bed in the intervertebral body. The entire disclosure is directed to production and use of a threaded intervertebral fusion implant. That implant, furthermore, is a bicortical dowel having an intermediate region composed of soft, porous cancellous bone, wholly inappropriate and too weak for use in the instant invention. The differences between cortical bone and cancellous bone implant healing are reviewed by Burchardt (Burchardt, 1983). There is no disclosure or suggestion of an interference screw made entirely of cortical bone.

Accordingly, there is a need in the art for a stable, strong interference screw made from cortical bone. This disclosure provides such a device, as well as methods for utilizing such a device.

BRIEF SUMMARY OF THE INVENTION

The novel interference screw of this invention is manufactured from cortical allograft bone to be used, for example, in fixation of cruciate ligament grafts. The interference screw of this invention has an immediate fixation strength that is comparable to metallic interference screws, and has the advantage of leaving no residual hardware while contributing to bone stock.

Accordingly, it is an object of this invention to provide an interference screw made from cortical bone.

Another object is to provide an interference screw made from bone which is capable of fusing with the bone into which it is implanted, thereby contributing to, rather than detracting from, bone stock in the area of the ligament or other implant.

Another object is to provide a self-tapping bone screw.

Another object is to provide a method for making an allograft interference screw.

Another object is to provide a method for using the allograft interference screw.

Other objects and aspects of this invention will become apparent from a review of the complete disclosure.

BRIEF SUMMARY OF THE FIGURES

FIG. 5D is a schematic of the finished screw of this invention.

FIG. 5J is a side view of a drive means.

FIG. 5K is an end-on view of the drive means shown in FIG. 5J.

DETAILED DESCRIPTION OF THE INVENTION

The method for preparing and using the interference screw of this invention comprises the steps of obtaining a fragment of bone from the cortex of an appropriate donor bone and machining the thread, tip and drive-head of the screw.

Figure 1A:
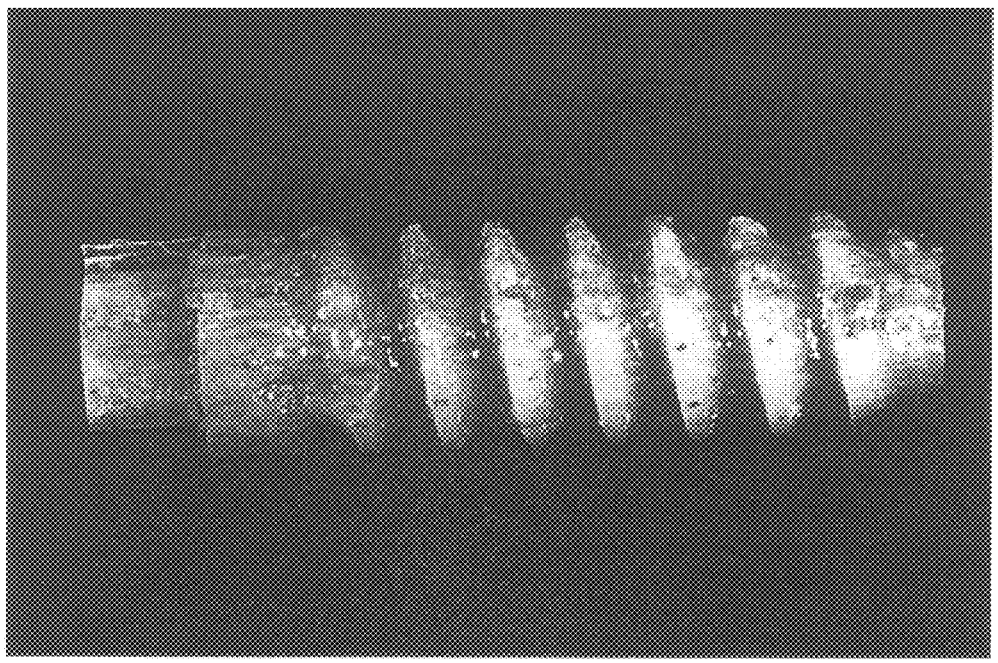
FIG. 1A is a photograph of one embodiment of this invention.
Figure 1B:
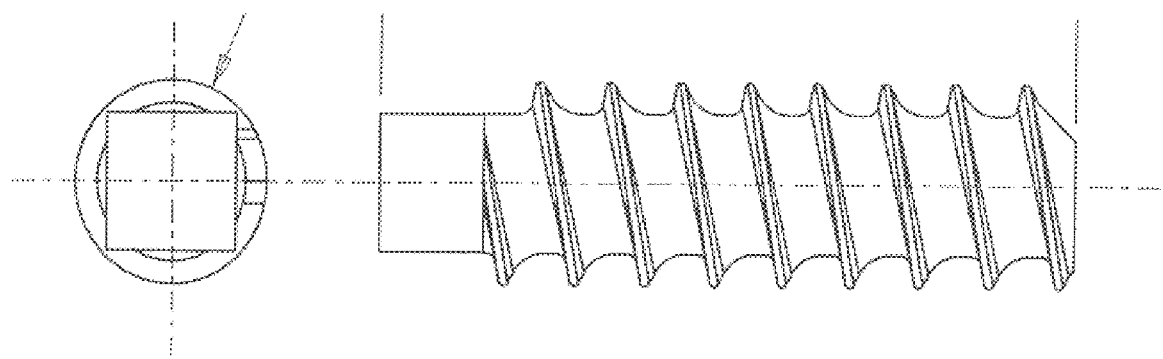
FIG. 1B is a schematic of the embodiment shown in FIG. 1A.

Referring to FIG. 1A, there is shown a photograph of an exemplary embodiment of the bone interference screw of this invention, and in FIG. 1B, there is provided a schematic of the same embodiment of the screw, showing several of the key dimensions of the screw. The length of this screw, as shown in FIG. 1B is about 25 mm, and the diameter, as shown in FIG. 1B, is about 7 mm. At one end of the screw, a square head is provided which matingly fits a square drive socket of an appropriate screw-driving implement. At the other end of the screw, there is provided a terminus which may be inserted into a pre-drilled cavity. The threads of the screw preferably cover approximately between about 75% and 95%, and most preferably about 85% of the length of the screw, with the remaining fraction of the screw being devoted to the drive-head.

It will be recognized by those skilled in the art that the drive-head may have any shape that allows sufficient torque to be applied to the head of the screw to drive the screw into a pre-drilled cavity of appropriate diameter. Accordingly, the drive-head may be square, as shown in FIGS. 1A and 1B, hexagonal, metric socket shaped or standard socket shaped. In addition, the head may have a machined, recessed Allen-wrench, star headed driver, phillips head or slotted head purchase for torque application. Furthermore, the drive recess may, for example, be that shown in U.S. Pat. No. 5,470,334, the disclosure of which is herein incorporated by reference, for receiving a rotatable driver. Furthermore, the threads of the screw of this invention may be of like dimensional arrangement to that shown in the U.S. Pat. No. 5,470,334. Likewise, the drive and thread arrangement disclosed in U.S. Pat. No. 5,364,400 is herein incorporated by reference as being acceptable and desirable for the bone interference screw of the present invention. Preferably, however, the thread will have a height of about 0.045 inches.

Accordingly, the bone screw of this invention may have a diameter between about 4 mm and about 12 mm, for ACL implant fixation, and preferably being about 5 mm, 7 mm, 9 mm, 10 mm or 11 mm in diameter. The length of the bone screw may be between about 8 mm and 70 mm, preferably being about 10 mm, 12 mm, 15 mm, 20 mm, 25 mm, 30 mm, or 40 mm in length. The same screw may be used for soft tissue attachment, with or without the addition of a flange being incorporated into the design of the head portion. Bone screws of this invention having appropriate length and diameter could also be used to advantage and with greater strength in applications such as, for example, the vertebral fusion procedure described by J. M. Vich (Vich, 1985), or it may be used to affix any number of other implants. For these differing purposes, it will be recognized that diameters as small as 4 mm and as large as 30 mm may be appropriate.

In every case, a consenting donor (i.e., a donor card or other form of acceptance to serve as a donor) is screened for a wide variety of communicable diseases and pathogens, including human immunodeficiency virus, cytomegalovirus, hepatitis B, hepatitis C and several other pathogens. These tests may be conducted by any of a number of means conventional in the art, including but not limited to ELISA assays, PCR assays, or hemagglutination. Such testing follows the requirements of: (i) American Association of Tissue Banks, Technical Manual for Tissue Banking, Technical Manual—Musculoskeletal Tissues, pages M19–M20; (ii) The Food and Drug Administration, Interim Rule, Federal Register/Vol. 58, No. 238/Tuesday, Dec. 14, 1993/Rules and Regulations/65517, D. Infectious Disease Testing and Donor Screening; (iii) MMWR/Vol. 43/No. RR-8, Guidelines for Preventing Transmission of Human Immunodeficiency Virus Through Transplantation of Human Tissue and Organs, pages 4–7; (iv) Florida Administrative Weekly, Vol. 10, No. 34, Aug. 21, 1992, 59A-1.001-014 59A-1.005(12) (c), F.A.C., (12) (a)–(h), 59A-1.005(15), F.A.C., (4) (a)–(8). In addition to a battery of standard biochemical assays, the donor, or their next of kin, is interviewed to ascertain whether the donor engaged in any of a number of high risk behaviors such as having multiple sexual partners, suffering from hemophilia, engaging in intravenous drug use etc. Once a donor has been ascertained to be acceptable, the bones useful for obtention of the screws as described above are recovered and cleaned.

The cortical sections are removed from linear aspects of the femur or from the anterior cortex of the tibia, and is preferably first machined into a dowel or "blank". A dowel of the cortical bone is then machined, preferably in a class 10 clean room, to the dimensions desired. The machining is preferably conducted on a graduated die, a grinding wheel, a lathe, or machining tools may be specifically designed and adapted for this purpose. Specific tolerances for the screws and reproduceability of the product dimensions are important features for the successful use of such screws in the clinical setting. A thread is cut on the circumference of the screw and a head cut to allow an appropriate driving tool to screw the interference device into a cavity machined by a surgeon, for example, adjacent to a ligamentous implant.

The forward end or tip of the screw which is to be inserted into a cavity formed by a surgeon adjacent the ligament or other implant is preferably fashioned by appropriate means known in the art, such as machining, to produce a tip of any desired geometry, such as a pointed tip, a rounded tip or a flush tip.

Preferably, opposite the forward end, a drive-head is machined, for example, by creating a square or hexagonal head. A square or hexagonal recess may also be drilled into the screw. It will be recognized by those skilled in the art that a number of shapes and modes of driving the screw into its implant site may be used, without departing from the invention disclosed and claimed herein. The final machined product may be stored, frozen or freeze-dried and vacuum sealed for later use.

Figure 5A:
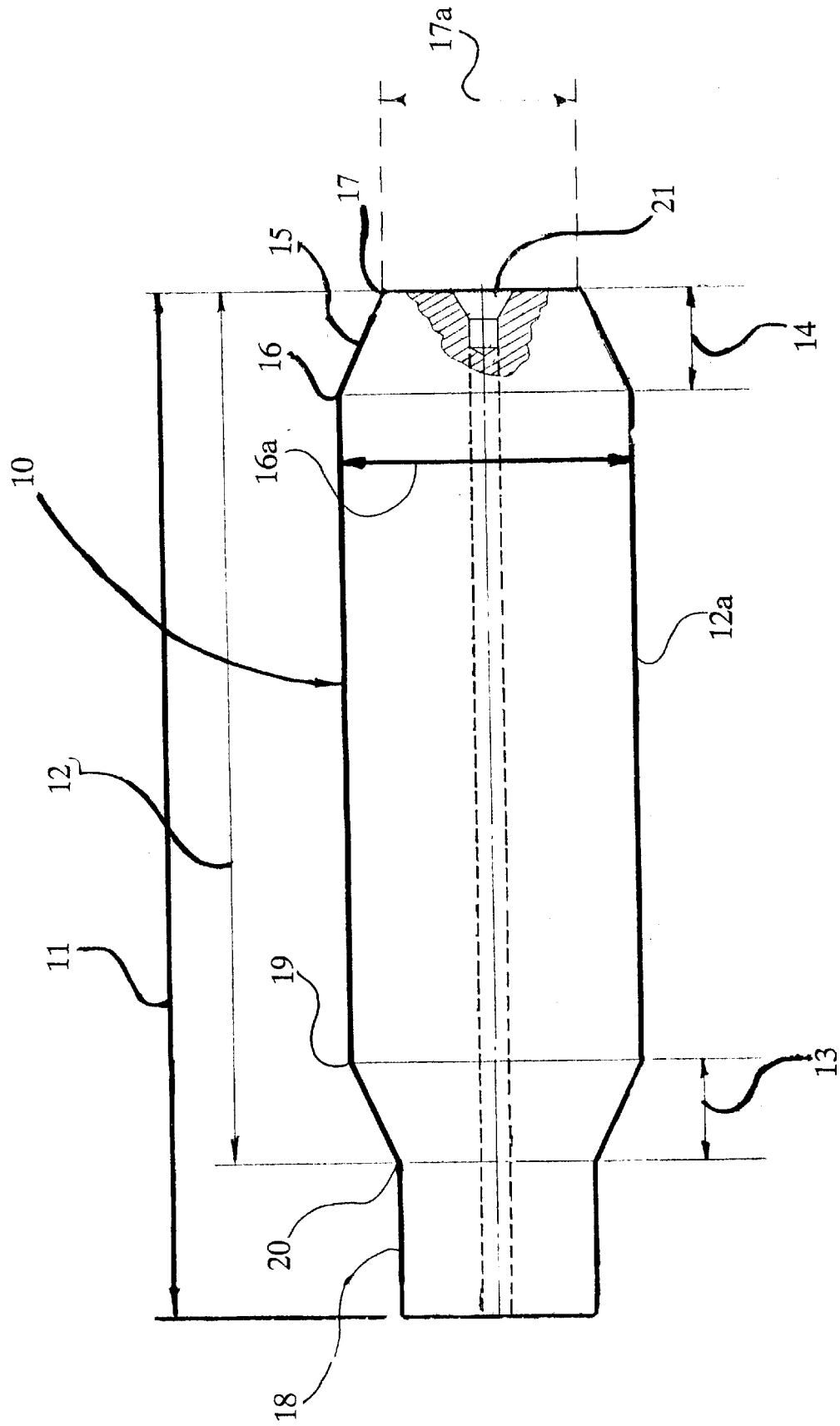
FIG. 5A is a schematic of a "blank" cortical dowel.
Figure 5B:
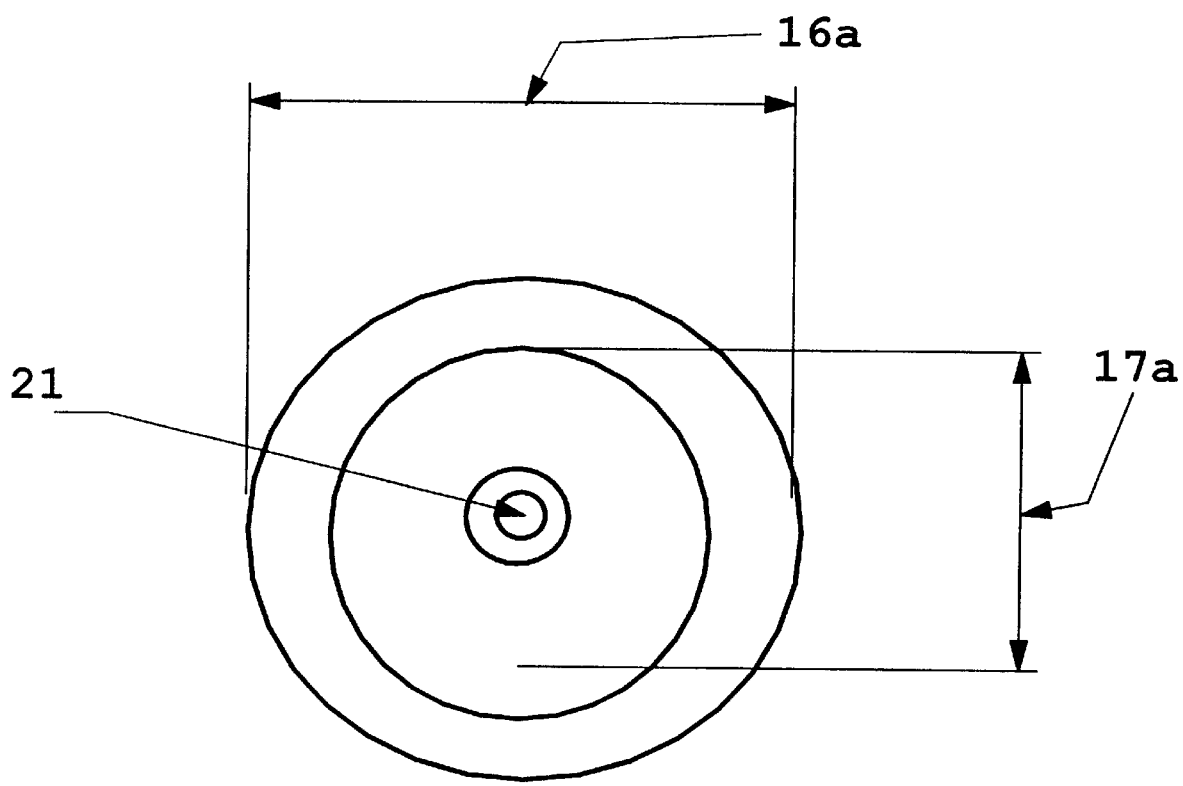
FIG. 5B is a head-on projection of the tip of the screw before machining the thread.

Referring now to FIG. 5A, there is shown a number of preferred features in a bone interference screw of this invention. In FIG. 5A, there is depicted a "blank", indicated generally by numeral 10, as produced prior to finishing. The blank's length is depicted by a first dimension 11, which is either in inches or is assigned a relative value of unity. A second dimension, 12 is provided, representing approximately 0.85 of the length 11. A third dimension, 13, and a fourth dimension, 14, are each provided, each representing approximately 0.10 of the length 11. A fifth dimension, 12a, is provided, representing the dimension 12 minus the dimensions 13 and 14. The forward end of the blank, 15, destined to become the "point" of the screw, has a tapered angle over the dimension 14, tapering from a diameter 16a of about 0.285 inches (which may also be assigned a relative value of unity and all other subsequently provided measurements being scaled appropriately) at point 16 to a diameter 17a of about 0.190 at point 17. At point 21, there is provided a centerdrill on the cylindrical centerline. The tapering and centerdrill at point 21 is shown in the head-on projection shown in FIG. 5B. This centerdrill is helpful in the machining of the screw. In addition, the centerdrill 21 may be extended throughout the dimension 11 as a centerbore in the screw to provide a cannulated screw. In this fashion, the screw may be guided into position by sliding the screw over a guide-wire, guide-pin or k-wire, all of which are conventional in the art. The centerbore of the cannulated screw need be no greater in diameter than about 0.5–3 mm, to avoid weakening the screw.

Figure 5C:
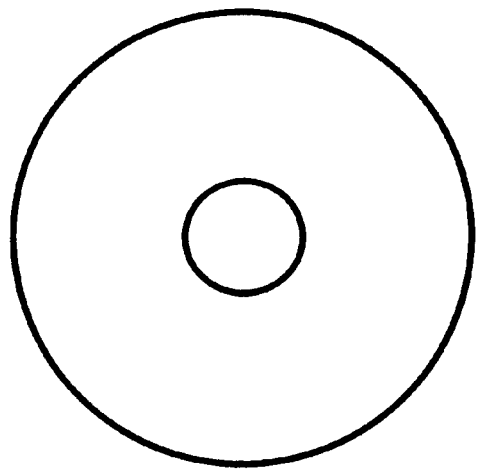
FIG. 5C is an end-on projection of the screw-head before machining into a drive head.

At the opposite end 18, destined to become the drive head of the screw, there is provided a tapered portion over the dimension 13, tapering from a diameter of about 0.285 at point 19 to a diameter 20a of about 0.191 at point 20. The end-on projection of FIG. 5C shows the diameter 20a of dimension 18, and the centerbore hole 21 concentric with the centerbore hole 21 of end 15.

The tapering of the screw blank, as described, is important to avoid the production of "feathery" edges upon machining of the thread. Such feathering may be encountered if a uniformly cylindrical blank is used to machine the thread.

In FIG. 5D, there is shown the screw after machining of the screw thread 22. The machined thread root diameter 23 is about 0.190 across the entire dimension 12. The thread crest diameter 24 over the dimension 12a is about 0.280 after machining. The crest diameter decreases over the dimensions 13 and 14.

The screw will preferably have a pitch of between about S threads per inch to about 40 threads per inch, and a diameter between about 2–15 mm, thereby defining the thread profile. With reference to FIG. 5E, those skilled in the art will recognize that the specifics of pitch (i.e., the distance 25a), diameter, and thread height 25 and shape will need to be adapted for the particular surgical application in which the screw is to be utilized. In one preferred embodiment, the diameter of the threaded portion of the screw is tapered, such that, for example, a screw having a length of 10–12 mm has a diameter which tapers from about 12 mm down to about 6 mm at the tip end of the screw.

Figure 5F:
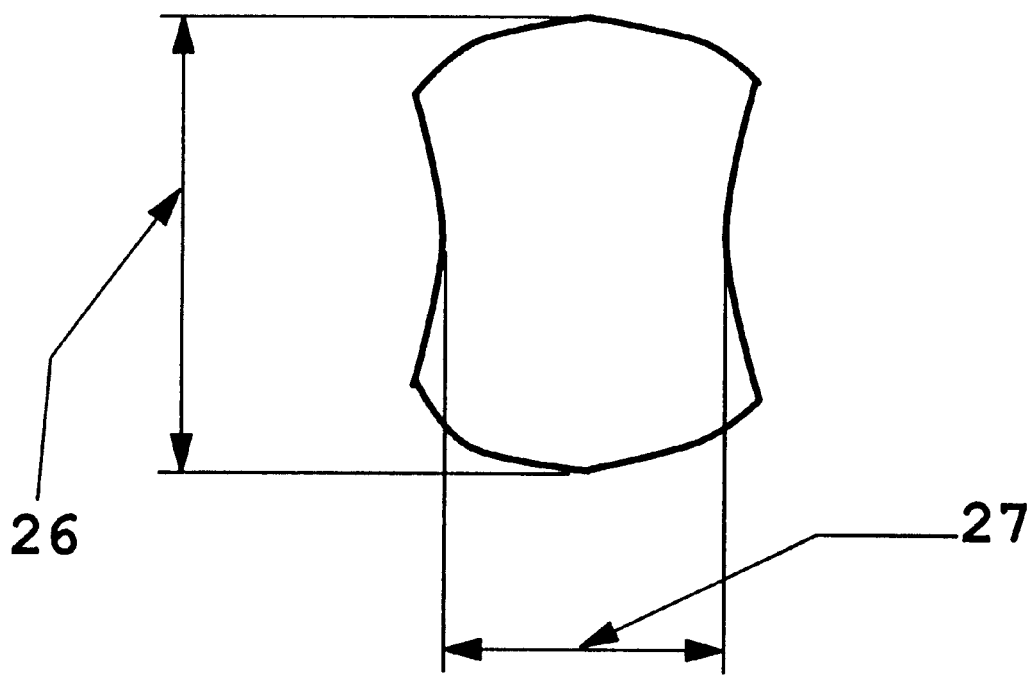
FIG. 5F is a representation of one embodiment of the screw head.
Figure 5E:
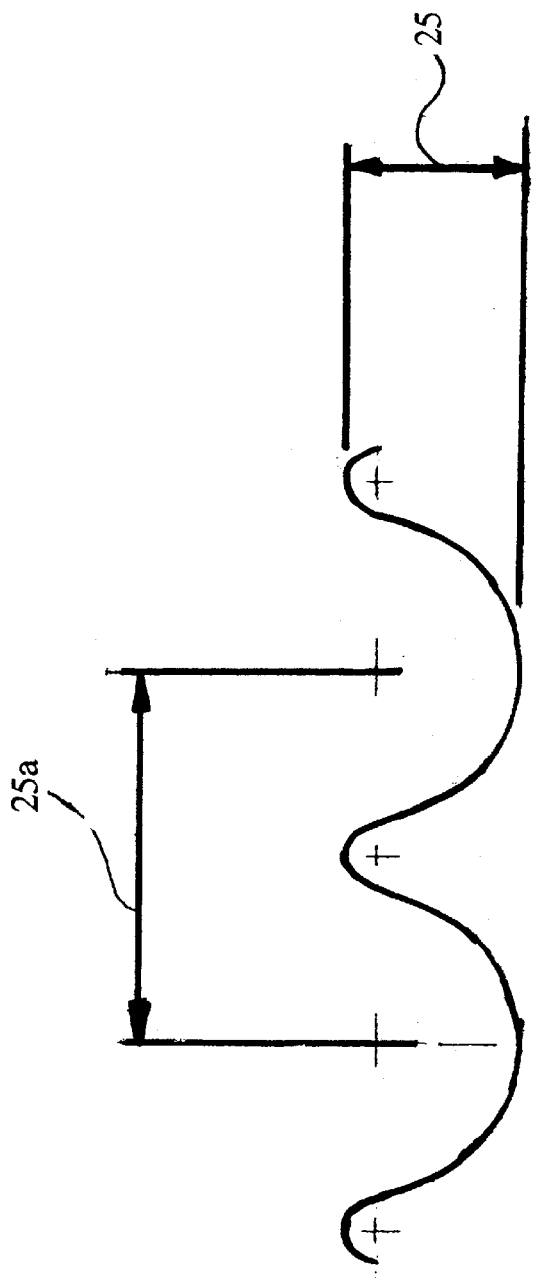
FIG. 5E is a detail of the screw thread.
Figure 5G:
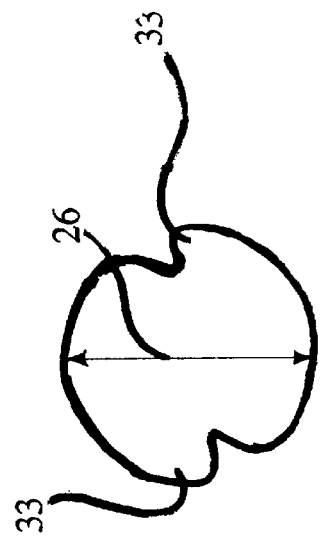
FIG. 5G is an alternate embodiment of the screw drive head.
Figures 5H, 5I:
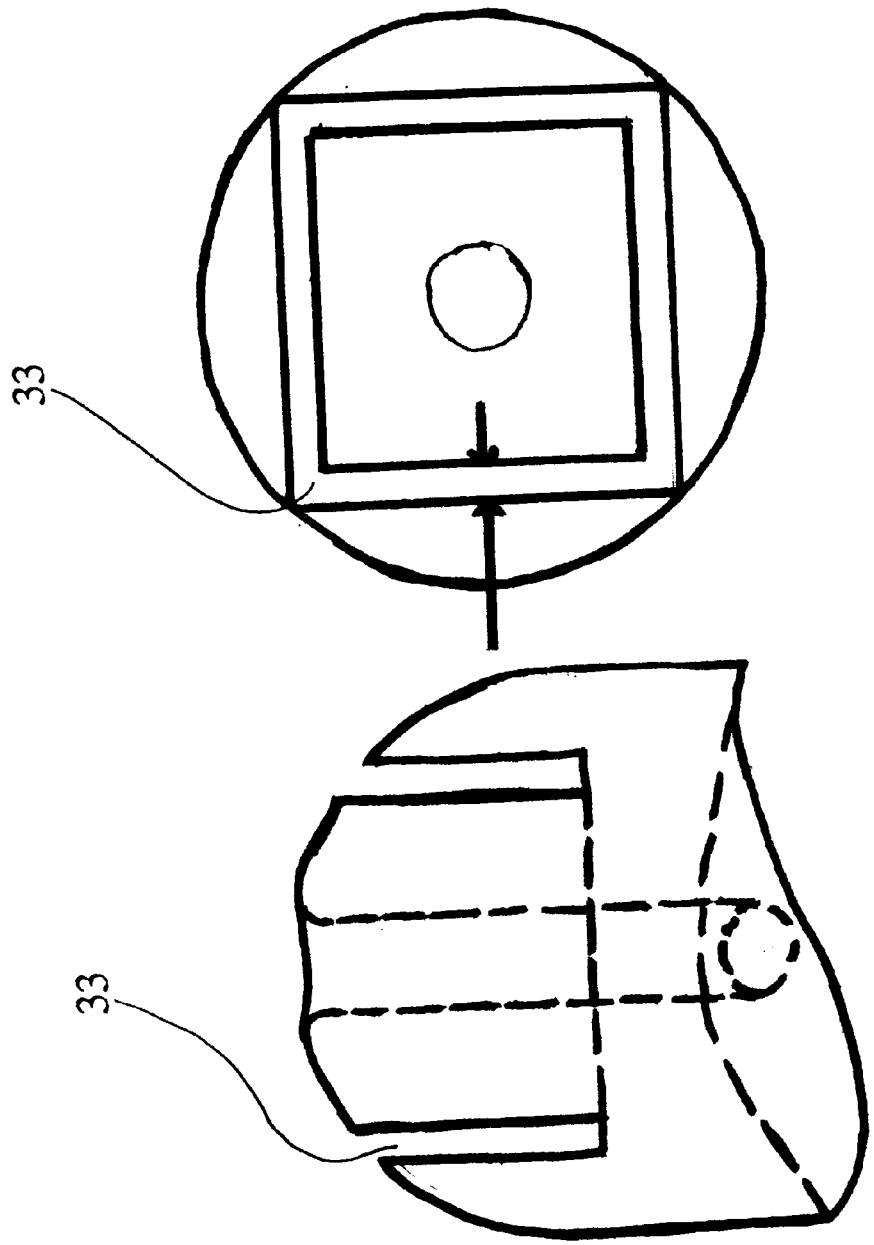
FIG. 5H is an alternate embodiment of the screw drive head.
FIG. 5I is a top view of the screw head shown in cross-section in FIG. 5H.

In FIG. 5F, there is shown a preferred machined head shape, referred to herein as a "dog bone-shape," thus providing a "dog bone-head screw". The diameter is machined to about 0.186 at dimension 26, and about 0.11 at dimension 27. No centerbore hole is shown as the cannulation is an optional albeit preferred embodiment. In FIG. 5G, there is shown an alternate machined head shape, referred to herein as a "twister" head having a pair of "wings", 33 which engage an appropriate drive means. In FIG. 5H, there is shown in cross-section a further head design, referred to herein as the "sunken groove" design. In this design a square groove 33 is drilled into the head of the screw. In a top view of the screw-head, FIG. 5I, there is shown the generally circular screw head with a square groove 33 drilled therein.

Accordingly, in a further aspect of this invention, there is provided a drive means optimized for driving a preferred dog bone-head shaped, twister-head shaped, or sunken groove head interference screw. FIG. 5J is a side-view of the driver showing a shaft 28 which may be turned by a handle or other means at 29. A recessed drive slot 30 is provided into which the dog bone-head or twister-head of the interference screw fits. Shown end-on in FIG. 5K are the drive slot, 30, and the shaft 28. The dog-bone shaped recess 30 engages the dog bone-head of the screw, to apply rotating torque thereto. For strength, the driver may be made from stainless steel, titanium or like material. Naturally, the driver is modified as required to mate with a twister-shaped head by fashioning the recess 30 to accommodate this shape. For the sunken groove head shown in FIGS. 5H and 5I, a rigid mating square headed drive means that fits into the machined square groove provides ample torque to insert that screw.

Figure 5L:
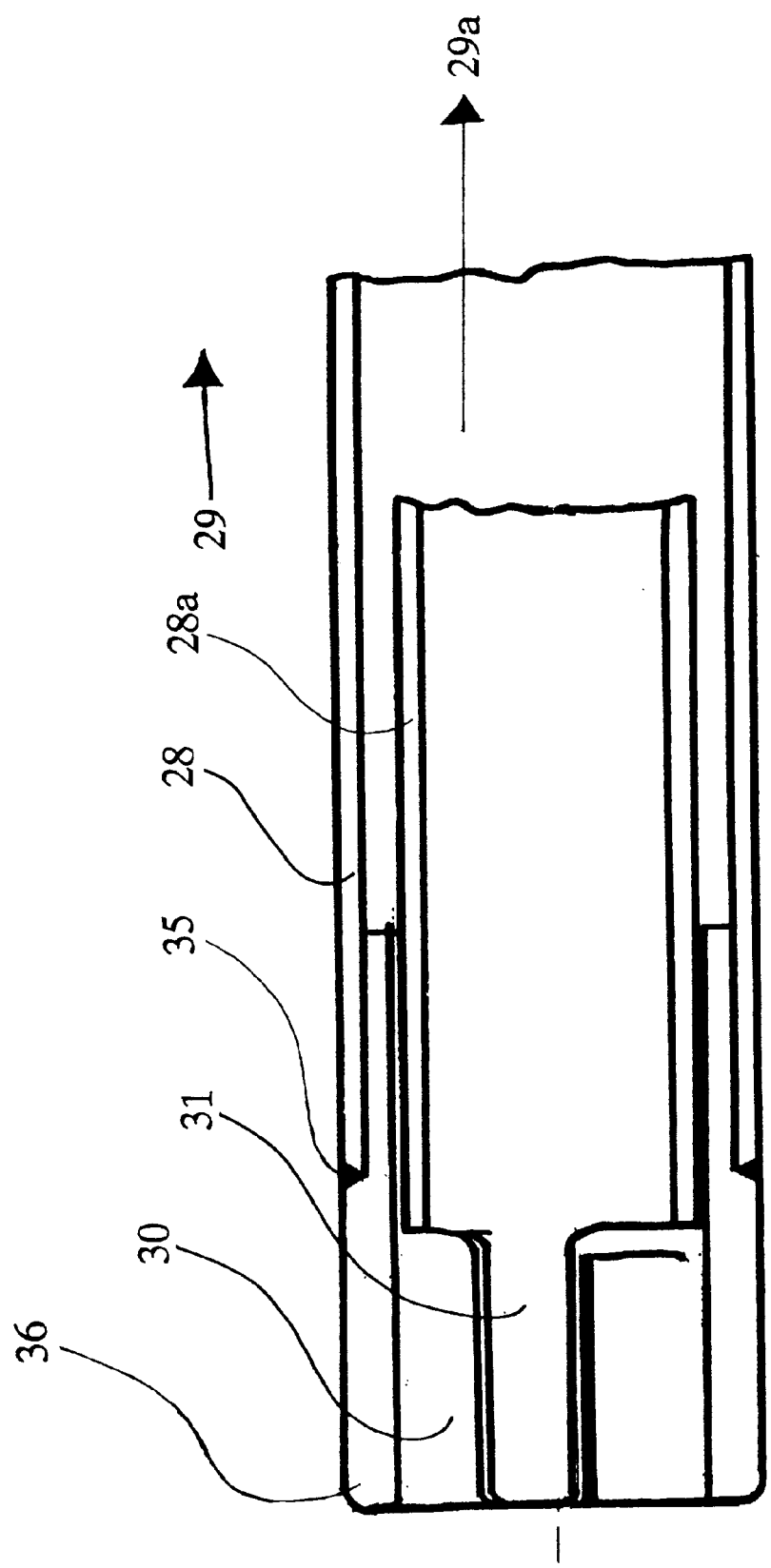
FIG. 5L shows a pinching drive means in cross-section.
Figure 5M:
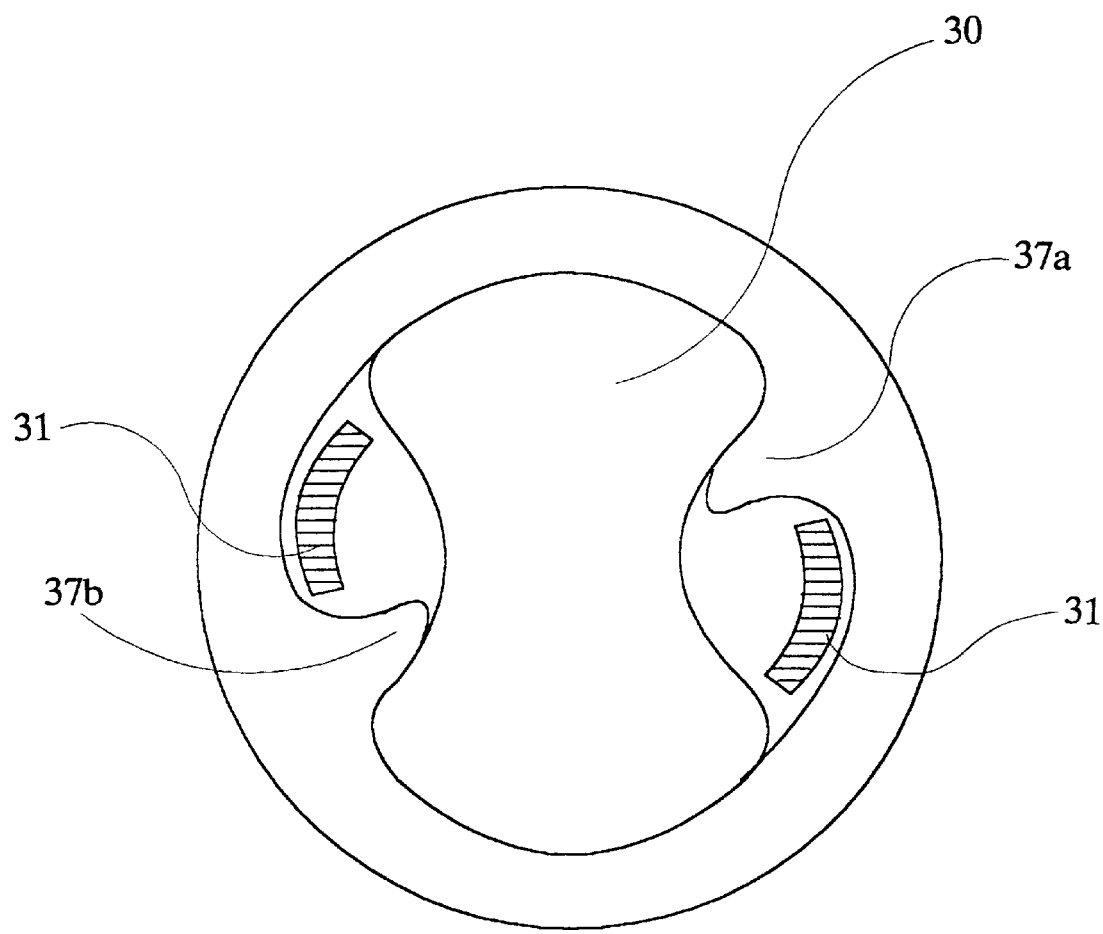
FIG. 5M is an end-on view of the driver means of FIG. 5K.
Figure 6A:
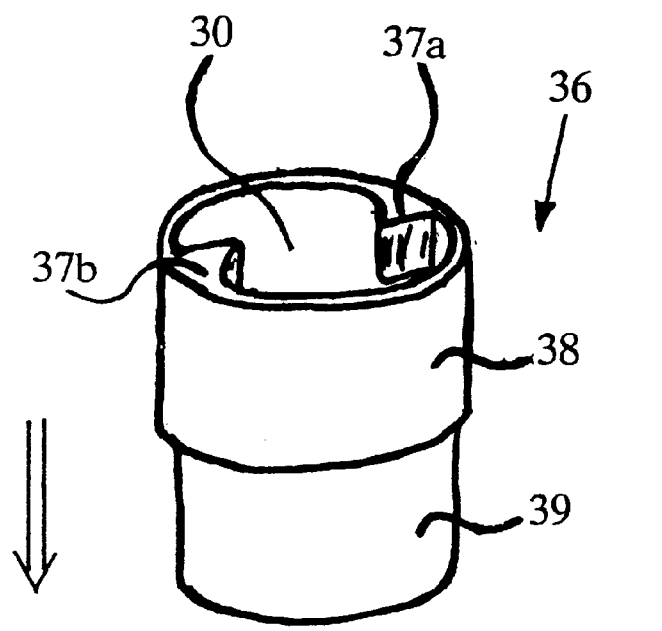
FIGS. 6A–6C is an exploded view of the driver means of FIGS. 5L and SM.
Figure 6B:
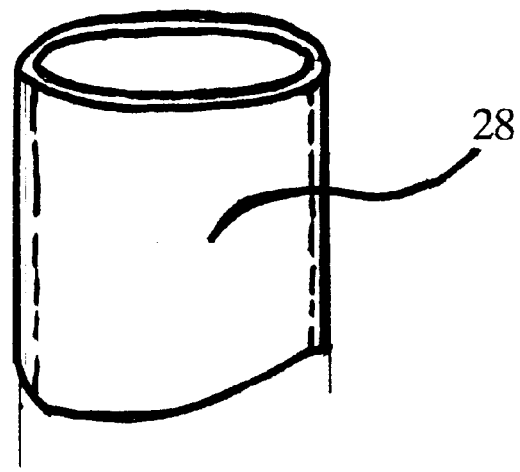
Figure 6C:
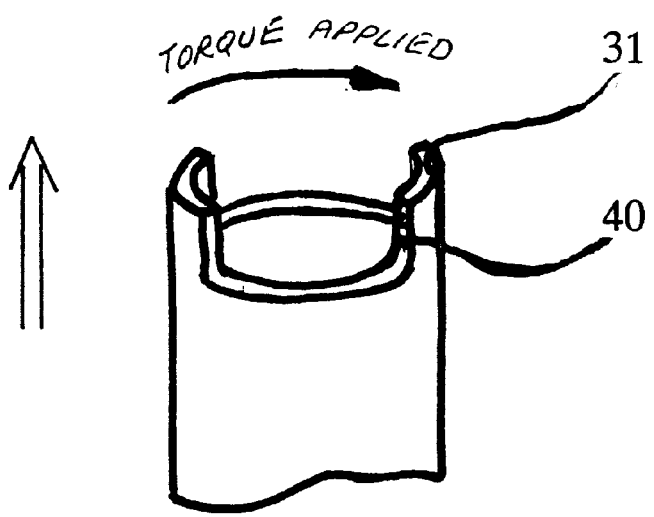

In an alternate embodiment of the drive means shown in FIGS. 5J and 5K, the drive means, shown in FIGS. 5L and 5M comprises (see FIG. 5L) an outer shaft 28, and an inner shaft 28a having a pair of forwardly projecting prongs 31, which extend into the recess 30. Attached to the outer shaft 28 is an outer shaft handle 29 (not shown) and attached to the inner shaft 28a is an inner shaft handle 29a (not shown). At point 35, an outer shaft insert 36 is welded into place. Viewed end-on, in FIG. 5M, the outer shaft insert 36 is seen to have a pair of inwardly projecting driver lugs 37a and 37b. In addition, the ends of the forwardly projecting prongs 31 are seen. This drive means is prepared, as shown in FIGS. 6A through 6C, by preparing an outer shaft insert 36 with a pair of inwardly projecting driver lugs 37a and 37b. The insert has an upper segment 38 with a first diameter that matches the diameter of the outer shaft 28. A second segment, 39, has a smaller outer diameter than that of the outer shaft 28, but an inner diameter that is still large enough to accommodate the inner shaft 28a. In this way, the outer shaft insert 36 may be inserted into the outer shaft 28 and welded at point 35, while the inner shaft 28a may be slid into the outer shaft 28 and still be rotatable therein. The outer shaft 28 is shown in FIG. 6B, and the inner shaft 28a is shown in FIG. 6C. The forwardly projecting prongs 31 optionally may have a serrated gripping surface 40. In operation, the bone-shaped head of a preferred screw of this invention is inserted into the drive recess 30. The driver lugs 37a and 37b will naturally engage the walls of the head of the screw. The outer shaft handle 29 is used to hold the screw as the inner shaft handle 29a is rotated slightly ("torque applied" in FIG. 6C) so that the forwardly projecting prongs 31 engage the opposite sides of the screw head to create a pinching action. The pinching action occurs because the prongs 31 force the screw head against the driver lugs 37a and 37b. The driver lugs 37a and 37b then are used to exert a torque in the opposite direction when the screw is screwed into the recipient's bone. The two handles may optimally interlock by an appropriate interlocking means to maintain the slight torque need to keep the screw head pinched. This embodiment of the driver is amenable to laporoscopic procedures where a screw may need to be "threaded" through tight spaces and orifices created in tissue. Advantageously, by removing the inner shaft 28a, the same drive head may be used to engage and drive the twister head screw.

Figure 7:
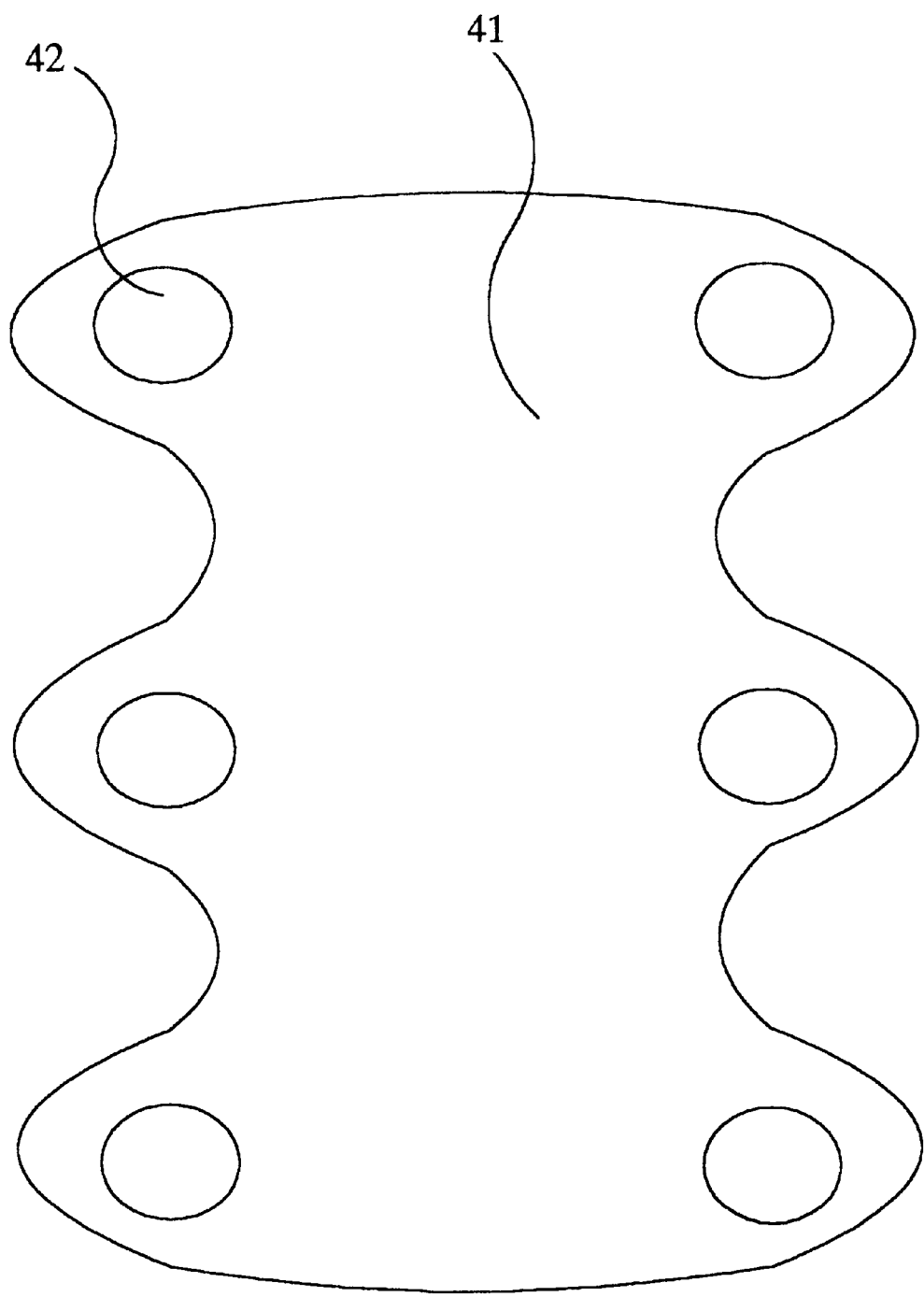
FIG. 7 shows a cortical bone fixation plate with screw holes machined therein.

In one laporoscopic procedure, the bone screw of this invention may be used to secure a standard titanium or like fixation plate as in a vertebral fusion. In FIG. 7, there is shown a design for a novel cortical bone plate 41 machined from cortical bone of tibia. Several screw holes 42 are shown in the plate. Advantageously, the interference screw of this invention is screwed through the screw holes 42 to hold the plate in appropriate fixation position so that adjacent vertebrae may be fused. For this purpose, it is preferred that the screw holes 42 be tapered, or counter-sunk so that once screwed into the screw hole, the screw head may be ground down so as to be flush with the surface of the bone plate. For this application, it is necessary for the head of the bone screw to have a greater diameter than that of the shaft of the bone screw or the hole in the bone plate, in order for the screw to provide a plate retention action. This is achieved by simply machining the bone screw to have a tapered head, as in a standard metal machine screw, such that once screwed into the bone plate, the top of the screw head is flush, thereby eliminating the need to grind down the screwhead. The entire fusion, including adjacent vertebrae, interference screws and bone plate all resorb over time as the fusion proceeds, and there is no need for subsequent removal of any hardware.

The clinical advantages of the instant bone interference screw are that it maintains bone stock, and there is no residual hardware as a result of use of the interference screw.

We have found that early motion and aggressive rehabilitation have led to improved results with anterior cruciate ligament reconstruction. The limiting factor in the early post-operative period is the initial fixation of the graft. The strength of the interference fit depends on the bone quality, compression of the plug within the tunnel, and contact between the screw threads and bone. Using the device of this invention and comparing its efficacy with standard metallic interference screws, no significant difference in pullout strength or mode of failure was observed.

Figure 2A:
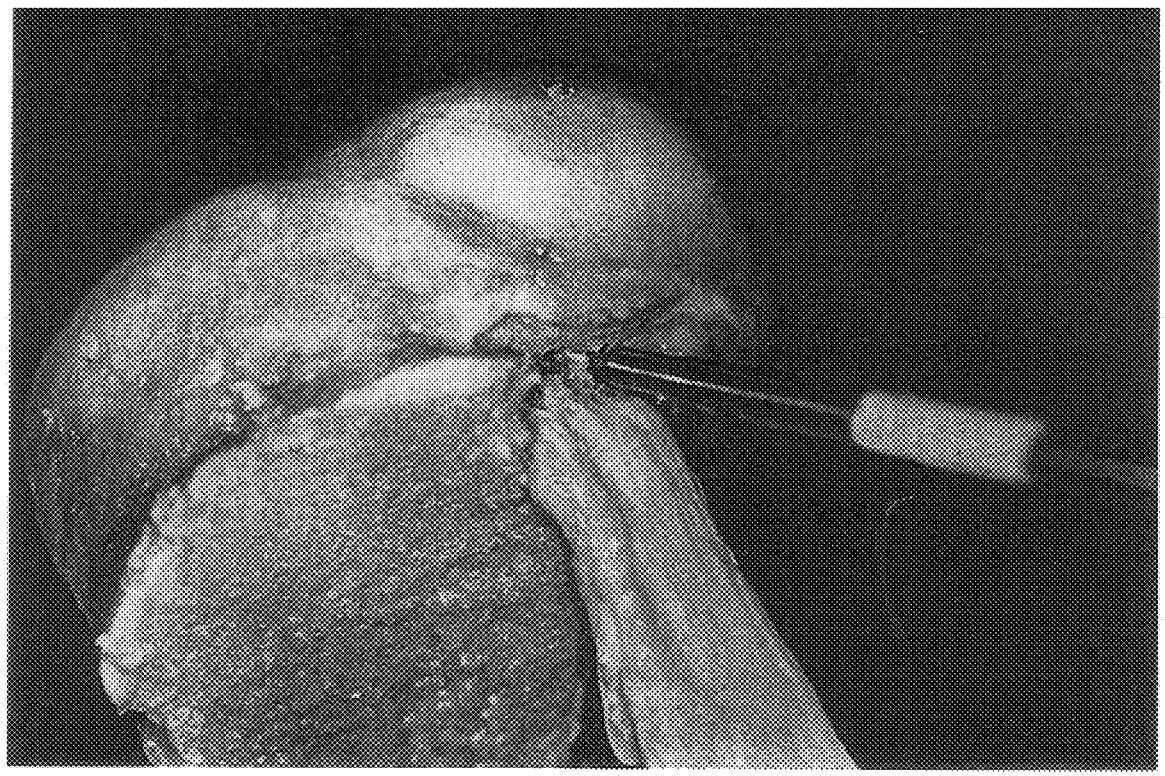
FIGS. 2A–2C show various stages in the use of a bone interference screw of this invention.
Figure 2B:
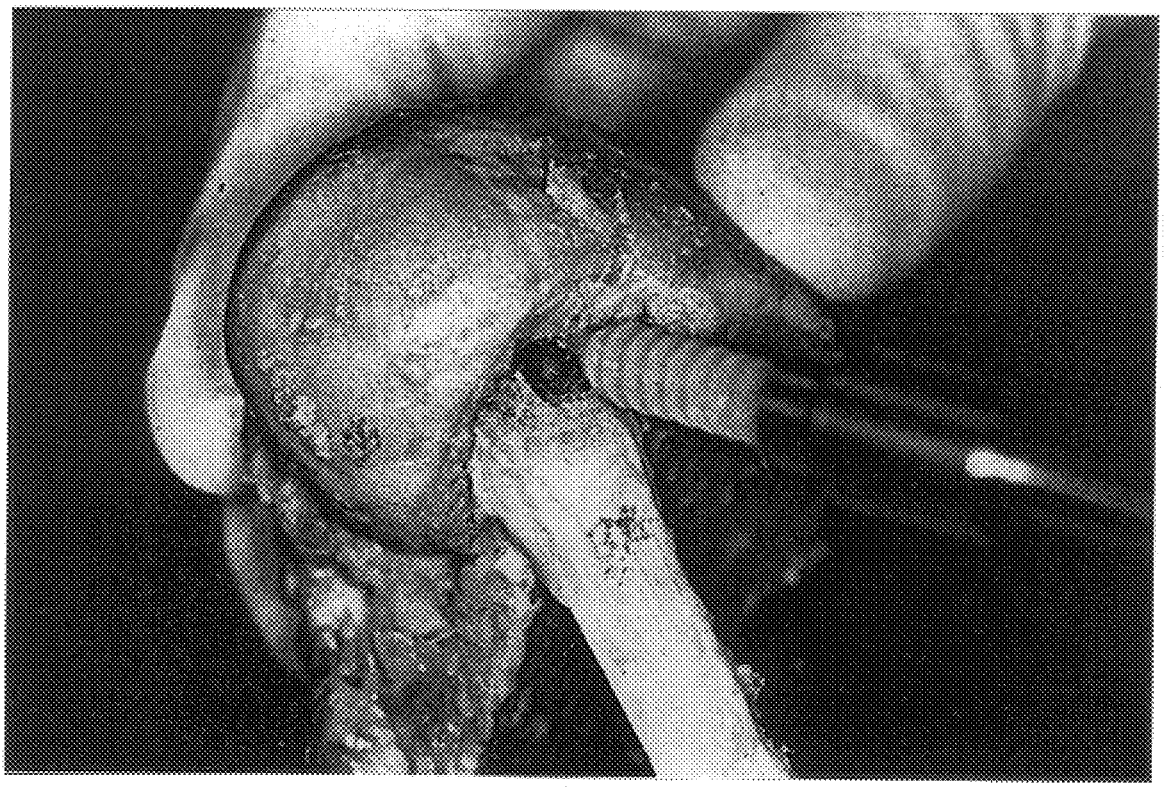
Figure 2C:
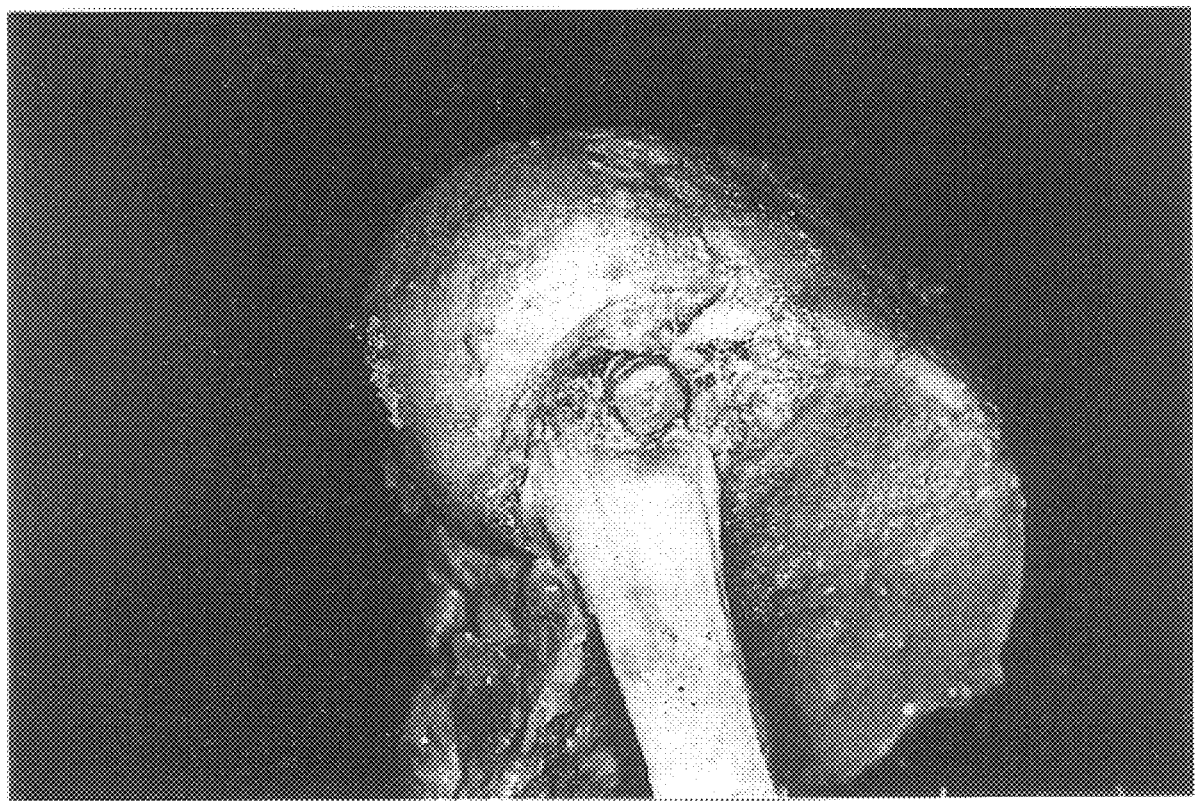
Figure 3:
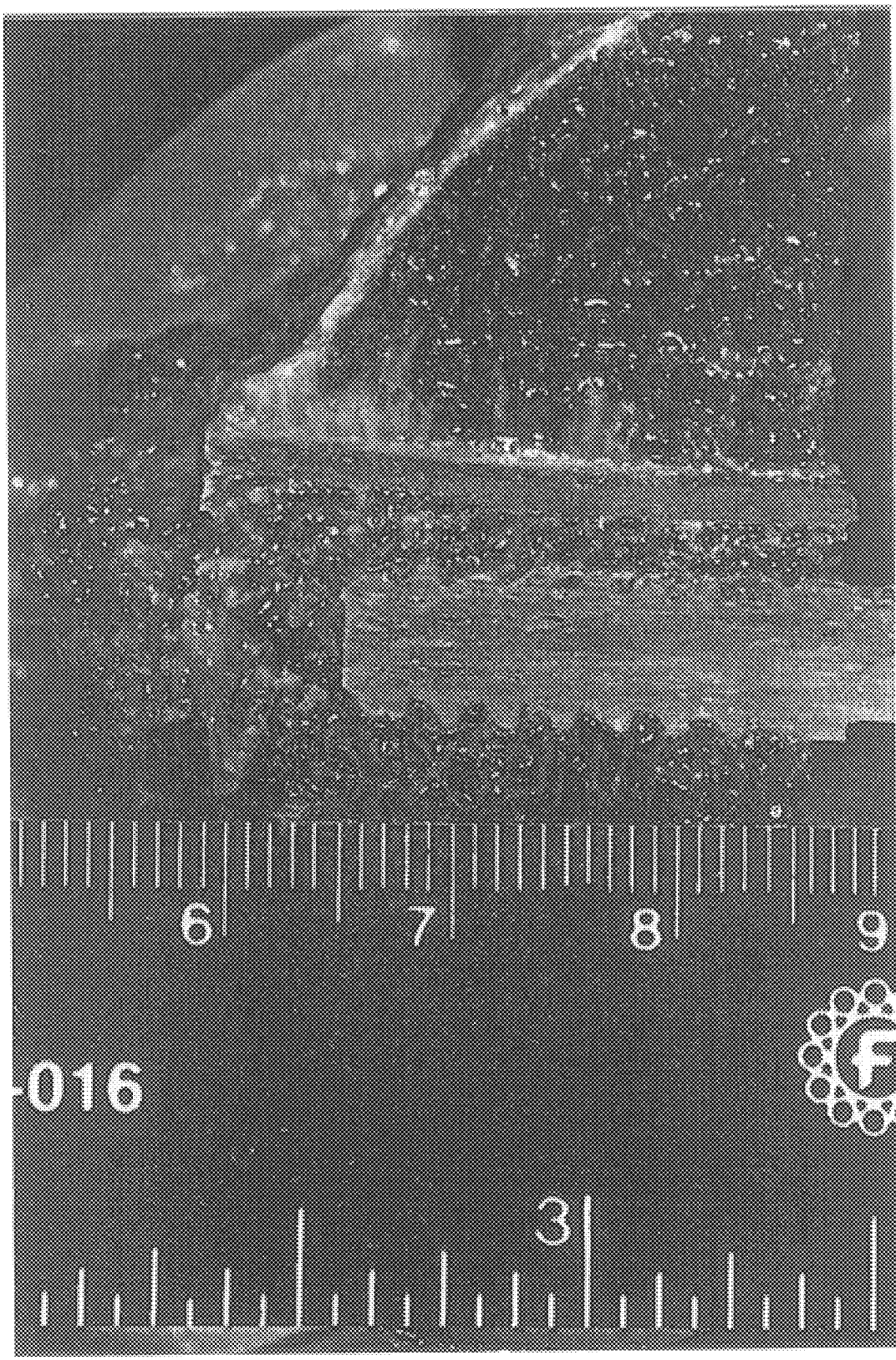
FIG. 3 is a cross-section of an implanted bone interference screw of this invention.

In use, for example in an ACL procedure, the surgeon creates a cavity for ligament implantation. A screw of this invention having the appropriate dimensions is selected by the surgeon, based on the needs of the particular patient undergoing the implant. As shown in FIGS. 2A–2C, the screw is mounted on an appropriate driver which has a drive-head that mates with the head machined on the screw opposite the pointed, rounded or flush forward end. The screw is carefully driven partially into the cavity created for insertion of the implant and partially into the solid bone adjacent to the implant which is thereby locked into place. The screw is driven until the drive-head is flush with the implant site. Over a period of several months, as shown in FIG. 3, it is found that substantial fusion of the screw to the bone into which it has been inserted occurs, without any dislodgement of the ligament implant. Various methods known in the art (see for example Boden and Schimandle, 1995) may be used to enhance fusion of implant bone.

While the foregoing description describes this invention, including its best mode, those skilled in the art will recognize that any of a number of variations on the basic theme disclosed herein can be made.

In a specific application utilizing one embodiment of this invention, seven allograft interference screws having dimensions of 7 mm by 25 mm were manufactured from the anterior cortex of fresh frozen human tibias. For comparative purposes, five conventional cannulated interference screws (7 mm by 25 mm) were used in parallel. Six fresh frozen human cadaveric femora were used for the implants. Patellar bone-tendon-bone grafts having a width of 11 mm with bone plugs of 25 mm length were implanted. A standard guide wire was placed in the condyle of the distal femur and an 11 mm reamer was used to drill over the wire. After placement of the bone plug, a pathway was fashioned for the allograft screw parallel to the plug using sequential dilators from 3 to 6 mm. Self-tapping allograft screws were placed with a custom socket driver for interference fit.

The implants were tested using an Instron Universal Testing Machine to test each specimen at a crosshead speed of 1 cm/min. The maximum force to failure as well as the mode of failure was documented for each specimen, and these data are reported in Table I:

TABLE 1

| Allograft screws (n = 7) | 627 N ± 205 N |
| Metallic screws (n = 5) | 803 N ± 244 N |

Figure 4:
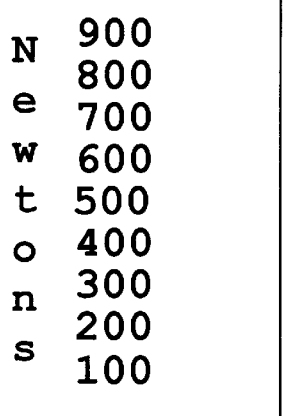
FIG. 4 is a graph showing the load to failure of bone as compared to metal interference screws.

Accordingly, this experiment demonstrated that there was no significant difference in the failure force (p=0.2) (see FIG. 4).

The pullout strengths shown above are consistent with those reported in several previous biomechanical studies using conventional interference screws.

Failure strengths have been reported between about 200 N and 600 N, with fixation dependent to some extent on screw size and the quality of the bone into which the screws are implanted.

The mode of failure is reported in Table II:

TABLE II

| Mode of Failure | | |
| --- | --- | --- |
| | Metal Screw | Allograft Screw |
| Screw pullout | 3 | 3 |
| Tendon-bone junction | 1 | 3 |
| Clamp failure | 1 | 1 |

Accordingly, no significant difference in the mode of failure is apparent.

What is claimed is:

1. A method for securing an implant which comprises drilling a cavity in an implant recipient's bone at or adjacent to an implant site and inserting therein an interference screw made from allograft or autograft cortical bone, thereby locking the implant into place, wherein the implant is a ligament implant in an anterior cruciate ligament surgical procedure.

2. The method of claim 1 wherein said interference screw is cannulated.

3. A method of repairing the anterior cruciate ligament in a patient which comprises:

creating a cavity for ligament implantation;
inserting a ligament implant in said cavity; and
inserting an interference screw into said cavity, adjacent to said ligament implant, said interference screw being made from a machined fragment of cortical bone.

* * * * *